United States Patent
Cau

(10) Patent No.: US 9,351,796 B2
(45) Date of Patent: May 31, 2016

(54) MICROSURGICAL ROBOT SYSTEM

(75) Inventor: Raimondo Cau, Eindhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 364 days.

(21) Appl. No.: 14/131,483

(22) PCT Filed: Jul. 12, 2012

(86) PCT No.: PCT/EP2012/063674
§ 371 (c)(1),
(2), (4) Date: Jan. 8, 2014

(87) PCT Pub. No.: WO2013/007784
PCT Pub. Date: Jan. 17, 2013

(65) Prior Publication Data
US 2014/0135794 A1    May 15, 2014

Related U.S. Application Data

(60) Provisional application No. 61/572,317, filed on Jul. 13, 2011.

(51) Int. Cl.
    *A61B 19/00*    (2006.01)

(52) U.S. Cl.
    CPC ............. *A61B 19/2203* (2013.01); *A61B 34/75* (2016.02); *Y10S 901/25* (2013.01); *Y10S 901/41* (2013.01)

(58) Field of Classification Search
    CPC ........ A61B 34/30; A61B 34/37; A61B 34/75; Y10T 74/20305
    See application file for complete search history.

(56) References Cited

U.S. PATENT DOCUMENTS

| | | | | |
|---|---|---|---|---|
| 6,024,576 A * | 2/2000 | Bevirt | ...................... | G05G 9/04 345/158 |
| 6,116,844 A * | 9/2000 | Hayward | ................. | B25J 9/106 414/680 |
| 8,282,653 B2 * | 10/2012 | Nelson | ................... | A61B 34/30 600/417 |
| 2005/0183532 A1 * | 8/2005 | Najafi | ...................... | A61B 8/00 74/490.01 |
| 2010/0192720 A1 * | 8/2010 | Helmer | ................ | B25J 17/0266 74/490.06 |
| 2010/0300230 A1 * | 12/2010 | Helmer | .................... | B25J 9/106 74/469 |
| 2012/0043100 A1 * | 2/2012 | Isobe | ................. | A61B 17/1631 173/42 |
| 2014/0135794 A1 * | 5/2014 | Cau | ..................... | A61B 19/2203 606/130 |
| 2015/0239133 A1 * | 8/2015 | Whitney | ................ | B25J 19/002 74/490.01 |

* cited by examiner

*Primary Examiner* — David M Fenstermacher
(74) *Attorney, Agent, or Firm* — Lumen Patent Firm

(57) ABSTRACT

Designs for modular microsurgical robotic devices and systems are provided, which could include one or multiple master-slave units coupled to a central microscope-based suspension structure. One of the main objectives is to provide robotic assistance during tasks which require long-term user concentration and high precision. The microsurgical robotic devices pay attention to motion scaling and tremor filtration in a 6 Degrees-of-Freedom (DOF) master-slave setup with force feedback. An extra DOF is included to actuate a 1-DOF instrument tip. Embodiments of this invention can be used in the medical environment as well as in other areas such as printed circuit board repair, watch and jewelry making, laboratory tasks, or other areas which require high precision over extended periods of time.

11 Claims, 15 Drawing Sheets

Conversion to mechanical elements for slave configuration

MICROSURGICAL ROBOT SYSTEM

CROSS-REFERENCE TO RELATED APPLICATIONS

This application is a 371 of PCT/EP2012/063674 filed on Jul. 12, 2012. PCT/EP2012/063674 filed on Jul. 12, 2012 claims the benefit of U.S. 61/572,317 filed on Jul. 13, 2011.

FIELD OF THE INVENTION

This invention relates to robotic systems. In particular, the invention relates to microsurgical devices and systems.

BACKGROUND OF THE INVENTION

Microsurgery demands a high degree of concentration and may put the performing surgeon in a physically strained position for the duration of the procedure. Some operations require accuracy close to the limit of human capability while others need to be finished within a certain time, putting a great physical as well as mental burden on these surgeons. Hence, the population of microsurgeons is relatively small compared to that of general surgeons. Meanwhile, microsurgery is one of the most trending fields of modern surgery, amongst which several reconstructive procedures and tissue transplantations. Most of these procedures have typical waiting lists of over 100 patients at any time, mainly due to capacity problems.

A microsurgical robot could provide a benefit in this field by increasing the surgeon capacity. A robotic system that offers motion scaling and tremor filtration lowers the threshold for surgeons to physically be able to perform microsurgery. A master-slave configuration allows for an ergonomically correct user interface, preventing the surgeon to sit in a strained position.

The present invention advances the art of robotic instrument manipulation devices and systems.

SUMMARY OF THE INVENTION

The present invention provides a design for a modular microsurgical robotic system including one or multiple master-slave units coupled to a central microscope-based suspension structure. One of the main functions of the system is to provide robotic assistance during tasks which require long-term user concentration and high precision. This is done by motion scaling and tremor filtration in a 6 Degrees-of-Freedom (DOF) master-slave setup with force feedback. An extra DOF is included to actuate a 1-DOF instrument tip. The primary field of application is in the medical environment; however the device can also be used in other fields with tasks having similar requirements. Accordingly, a similar device could also be used for similar applications in a different field, such as printed circuit board repair, watch and jewelry making, laboratory tasks, etc.

The kinematic properties of the master and slave units are based on the anatomy of a human hand holding a microsurgical instrument, which makes the dynamic behavior of the system highly intuitive for microsurgeons. The predictability of the motion trajectories of the slave unit makes it possible to use the system in a multi-person setup. Also, it reduces the amount of preliminary training required to operate the device.

The structural layouts of the master and slave units are identical and highly symmetrical, which is one of the unique design features of the system. By using a virtual wrist joint and an extended parallelogram the units are balanced against gravitational pull. Each master or slave unit has six active degrees of freedom, which are formed by serially placing three differential gears along the extended parallelogram layout. Each differential gear is contained by a differential module built of two identical halves, each able to function independently. This creates a system that is easy controllable, robust, and cost-effective.

The suspension structure serves as a central docking station for the slave devices and can display information about the status of the system. The system can also be designed as a compact workstation with a fixed operating plane and integrated microscope.

The system makes use of true microsurgical instruments, which are coupled to the slave device and can be actuated by a set of jaws. Moreover, other applications include micromanipulation in precision.

The present invention further provides a robotic instrument manipulation device with three modules, a first module, a second module and a third module.

The first module has a top portion and a bottom portion. The top portion of the first module has a first differential gear. The bottom portion of the first module has a universal joint. The first differential gear has a first driven gear and a first pair of driving gears disposed on opposite sides of the first driven gear. The first pair of driving gears are disposed along a first common axis. The first driven gear has a first drive shaft that is fixedly suspended.

The first module rotates about an axis of the first drive shaft when the first pair of driving gears counter rotate. The first driven gear rotates the first module about the first common axis when the first pair of driving gears co-rotate.

The second module has a top portion and a second portion. The top portion of the first module is pivotably connected to the top portion of the second module. This pivotable connection includes a first module pivotable connection and a second module pivotable connection.

The bottom portion of the second module has a second differential gear. The second differential gear has a second driven gear and a second pair of driving gears disposed on opposite sides of the second driven gear. The second pair of driving gears are disposed along a second common axis. The second driven gear has a second drive shaft that rotates about an axis of the second drive shaft when the second pair of driving gears counter rotate. The second drive shaft rotates about the second common axis when the second pair of driving gears co-rotate.

The third module has a proximal end and a distal end. A third differential gear is disposed at a distal end of the third module. The distal end of the second drive shaft is fixedly connected to a proximal end of the third module. A midportion of the second drive shaft is universally connected to the universal joint.

The third differential gear has a third driven gear and a third pair of driving gears disposed on opposite sides of the third driven gear. The third pair of driving gears are disposed along a third common axis. The third driven gear could have an instrument such that the instrument rotates about the instrument's longitudinal axis when the third pair of driving gears counter rotate. The instrument could rotate about the third common axis when the third pair of driving gears co-rotate. The instrument could be an actuator, whereby the actuator operates a tool disposed at a distal end of the instrument.

The first module pivotable connection, the second module pivotable connection, the second common axis and the universal joint form a parallelogram. In one example, the pivotal connection between the top portion of the first module and the top portion of the second module could be a rigid link of the parallelogram.

In one example, the robotic instrument manipulation device could have a center of gravity that is proximal to the universal joint.

In another example, the robotic instrument manipulation device could be remotely controlled according to a master-slave system. A master device in the master-slave system could be a second robotic instrument manipulation device that is operated using a tool on the instrument.

In yet another example, first module pivotal connection could include the first common axis of the first differential gear. In this example, the pivotal connection between the top portion of the first module and the top portion of the second module could further be a rigid link of the parallelogram, whereby the rigid parallelogram link is perpendicular to the first shaft.

In still other examples, the first common axis could be perpendicular to the first drive shaft, the second common axis could be perpendicular to be second drive shaft, and/or the third common axis could be perpendicular to the third drive shaft.

DETAILED DESCRIPTION

Kinematics

Figure 1:
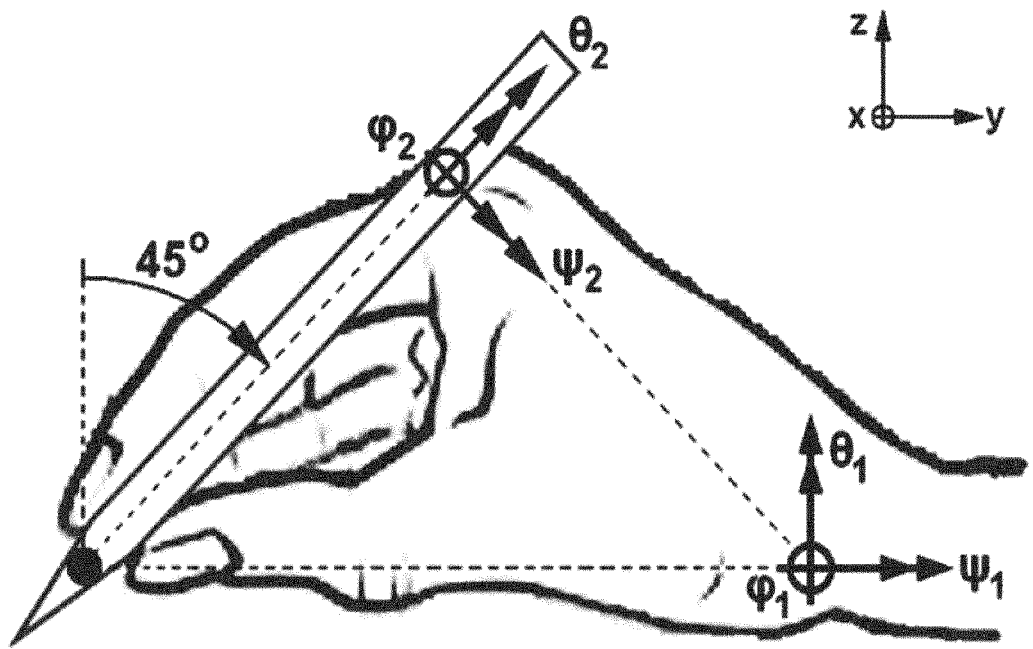
FIG. 1 shows a recommended microsurgical instrument grip according to an embodiment of the invention.

The range of motion and kinematics of both the master and slave design are based on the anatomy of a human hand holding a pen shaped object, with the wrist joint being a fixed point in space and the tip of the pen being the end effector (FIG. 1). It is a unique feature that makes master and slave have similar kinematics. This implies that the design has 6-DOF, being one spherical joint at the wrist and another at the base of the index finger where the pen is supported. This is the natural and recommended grip for surgeons to hold a microsurgical instrument, whereas the instrument shaft makes a 45 degree angle with the operating plane (FIG. 1).

The spherical joint at the wrist is used to make large motions with relatively low accuracy, while the spherical joint at the fingers is used to make smaller motions with high accuracy. In practice, when holding a pen the freedom of movement of the rotations of the spherical joint at the fingers is limited to a few degrees. It can be assumed that in that case rotation $\psi 2$ and $\psi 1$ are lined up and behave as one.

This principle has been translated to a kinematic design that is suitable for both the master and slave unit.

Figure 2:
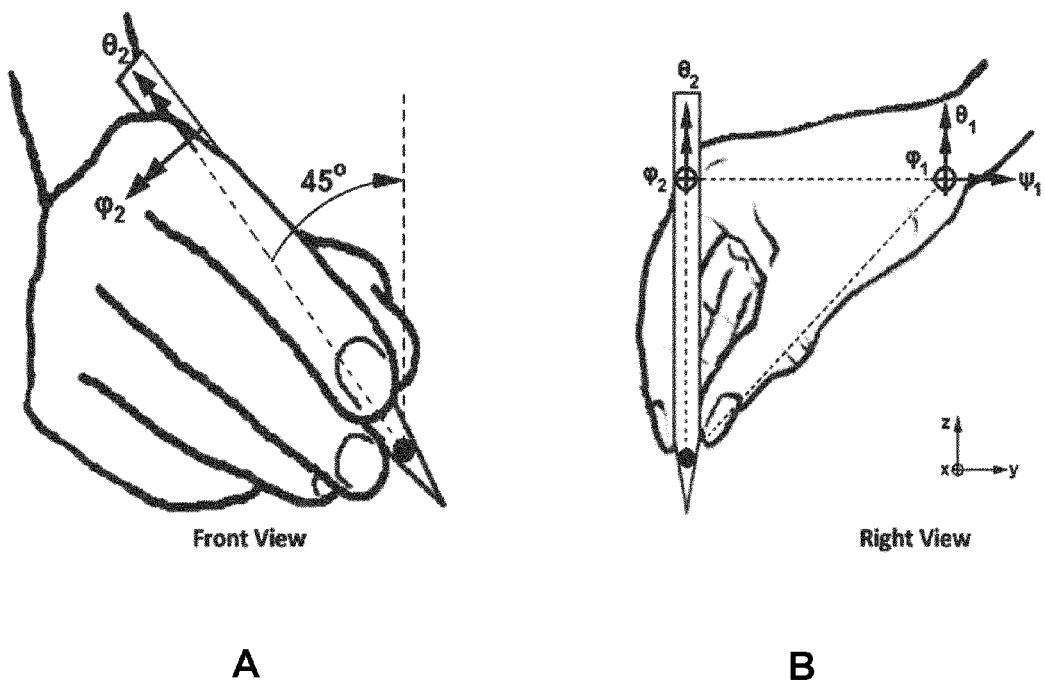
FIGS. 2A-B show a front (A) and right (B) view of the adjusted instrument grip used for the slave design according to an embodiment of the invention.

In the slave configuration, the wrist joint is translated upwards until the instrument shaft is vertically aligned with the tip and $\psi 1$ is aligned with $\psi 2$. The Instrument shaft is then tilted sideways to a 45 degree angle of attack toward the operation plane (FIGS. 2A-B).

For the slave design, moving the wrist joint upwards provides lower clearance on the operating plane, to make room for e.g. surgical accessories and free flaps around the operation site and provide a direct sight on the procedure. Tilting the instrument shaft provides center clearance for the microscope's field of view.

Next, the spherical joint at the wrist is expanded as depicted in FIGS. 3A-B.

Figure 3:
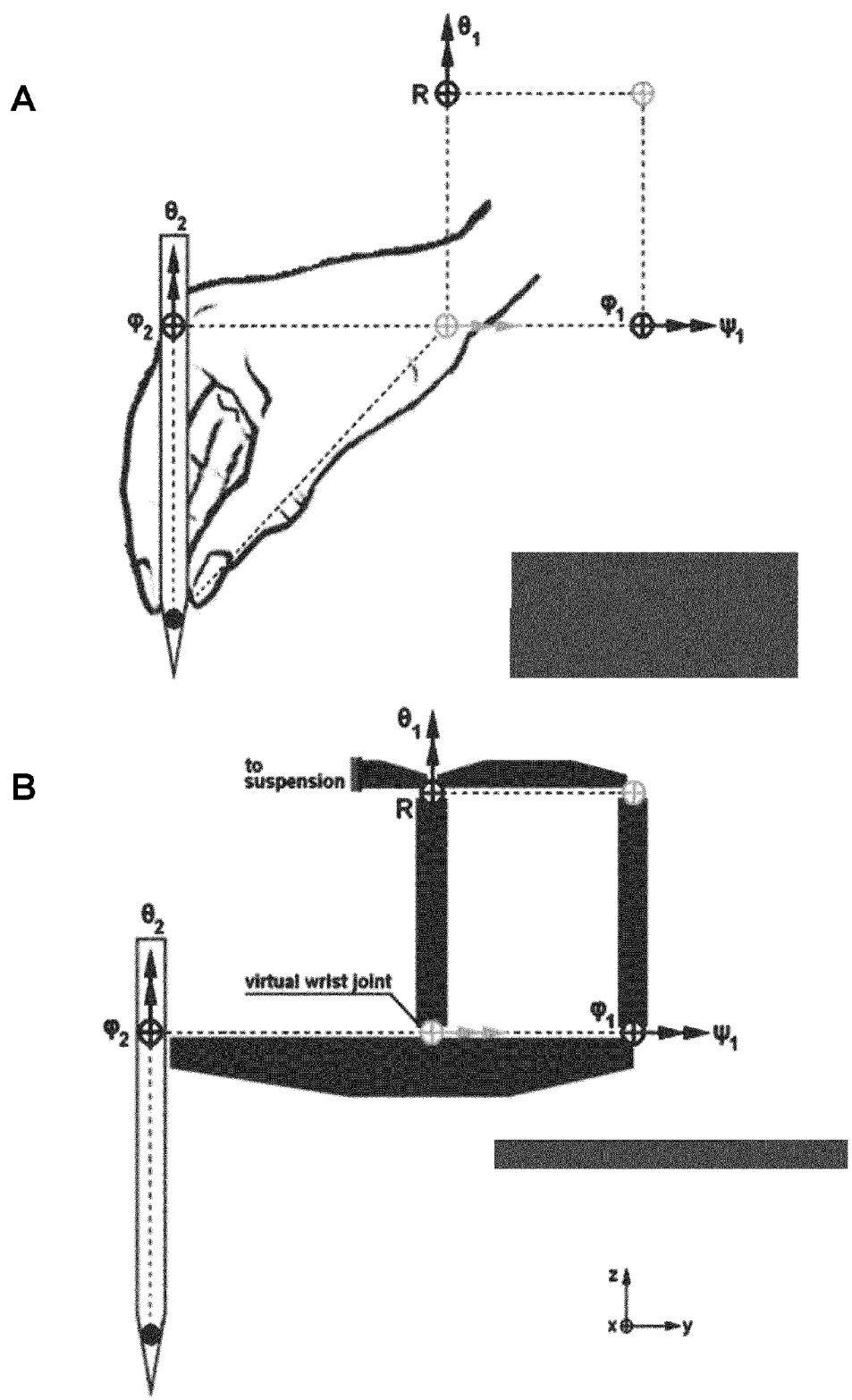
FIGS. 3A-B show an expansion of the wrist joint and addition of extended parallelogram according to an embodiment of the invention.

Rotations $\psi 1$ and $\phi 1$ are moved backwards while $\theta 1$ is moved further upwards, creating a virtual ball joint at the wrist (FIG. 3). Moreover, a vertically orientated parallelogram is introduced behind the virtual wrist joint, actuated both by R and $\phi 1$.

The parallelogram configuration provides a number of design benefits.

Figure 4:
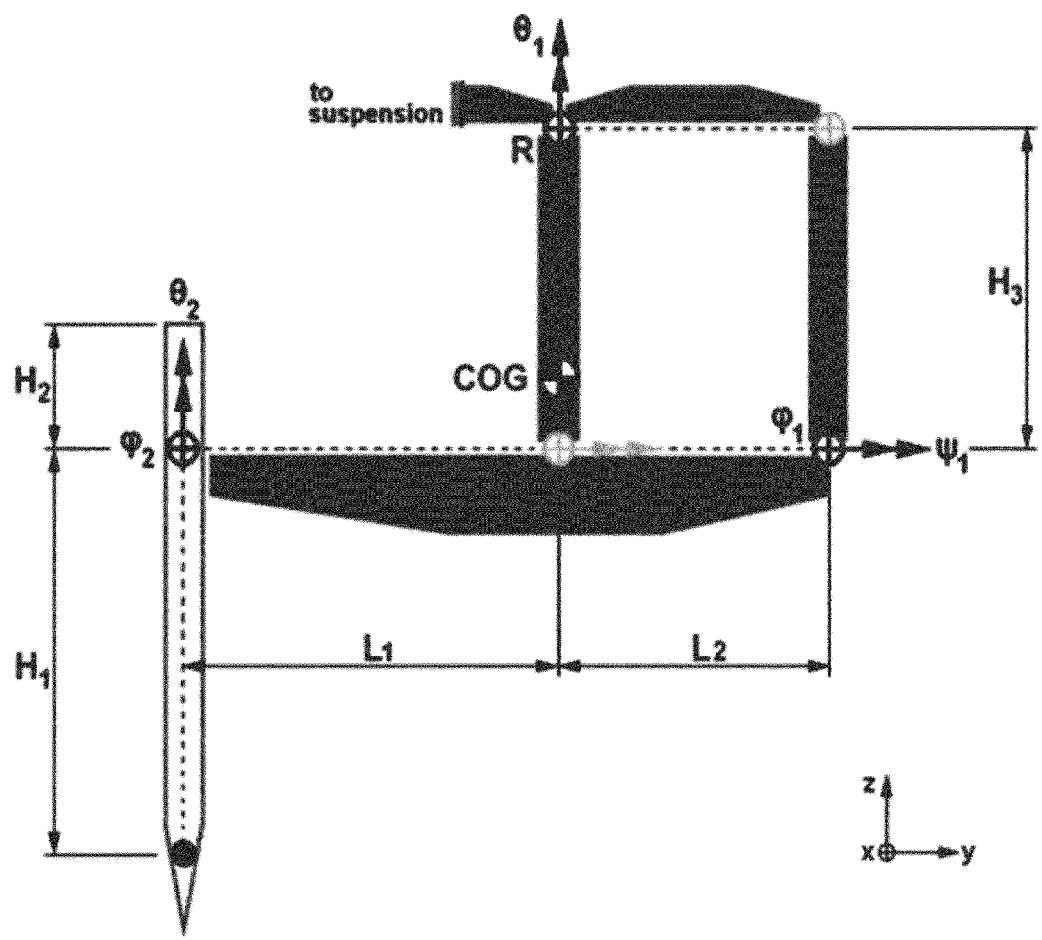
FIG. 4 shows an example of balancing and center of gravity (COG) according to an embodiment of the invention.

Lengths L1 and L2 can be adjusted such that the y-component of the center of gravity (COG) of the structure lies on a vertical plane going through the virtual wrist joint (FIG. 4). A design symmetrical through the z-y plane will make sure the x-component of the COG lies in the virtual wrist joint. The z-component of the COG then lies on a vertical line between the suspension and the virtual wrist joint, thus forcing the structure to a static equilibrium point around R. All other rotations can be balanced against gravitational pull.

Heights H1 and H3 can be chosen such that the bottom of the device and the suspension are positioned adequately high above the operation site. Height H2 is an extension of the instrument shaft and can be equipped with a balancing weight, e.g. a dc-motor for instrument tip actuation.

Figure 5:
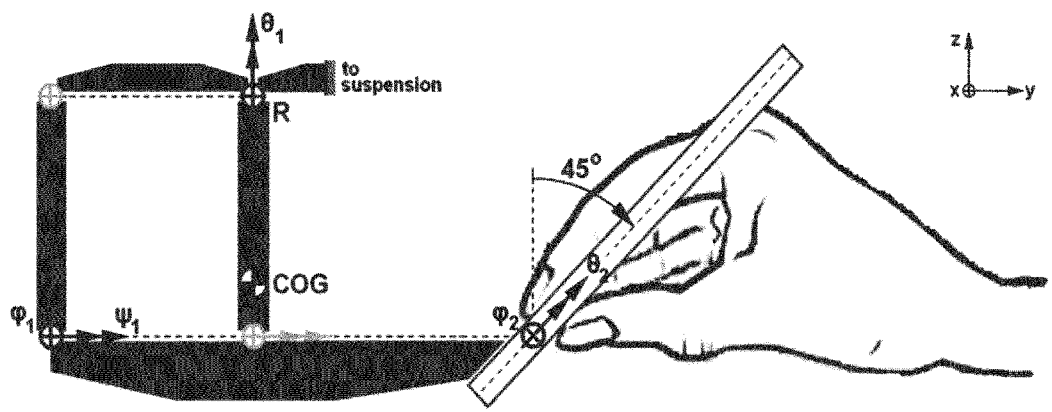
FIG. 5 shows a mechanical layout for master configuration according to an embodiment of the invention.

The master device makes use of the same parallelogram configuration, the only difference being the position and orientation of the instrument shaft (FIG. 5).

The hand is now in the same position as depicted in FIG. 1, the recommended surgical instrument grip. Rotation $\psi 1$ is aligned with the axis of rotation of the lower arm of the user (FIG. 5). The other coarse movements from the user's wrist are converted by rotations $\theta 1$ and $\phi 1$. The finer movements coming from the fingers are translated into rotations $\phi 2$, $\theta 2$ and R.

Suspension

The suspension design for both master and slave units has been made adaptable to selected surgical procedures. In an operating room it is vital that devices do not take up more space that absolutely necessary. Since some operations require more robotic assistance than others (e.g. single or multi-person), the system has been made modular. The suspension structures are built around existing components in the operating room, such that they do not conflict with the customary procedures and can easily be removed.

Figure 6:
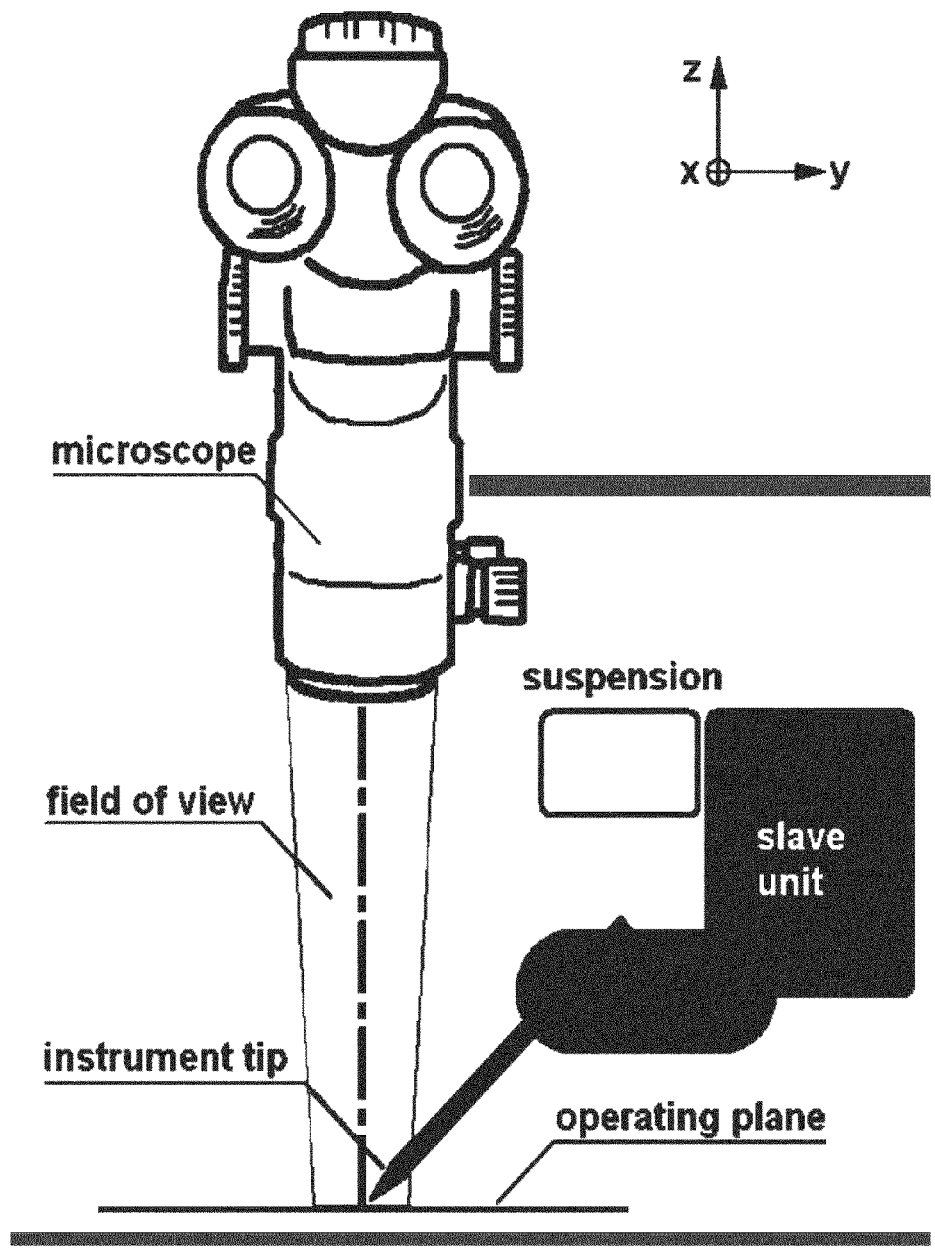
FIG. 6 shows a position of slave suspension with respect to microscope according to an embodiment of the invention.

For a master-slave system in microsurgery, the slave unit suspension will be microscope based. This implies that the slave unit suspension is positioned with respect to the microscope (FIG. 6), such that the field of view of the microscope encompasses the slave unit instrument tip at all times.

Since the device is meant to be suitable for multi-person usage, there can be several slave units operating simultaneously on the operating plane using the same microscope.

Hence, the suspension should be designed as a structure containing a center clearance for the microscope's field of view. The suspension must be able to contain several slave units, which can independently be positioned with respect to the microscope and can be removed when necessary.

Figure 7:
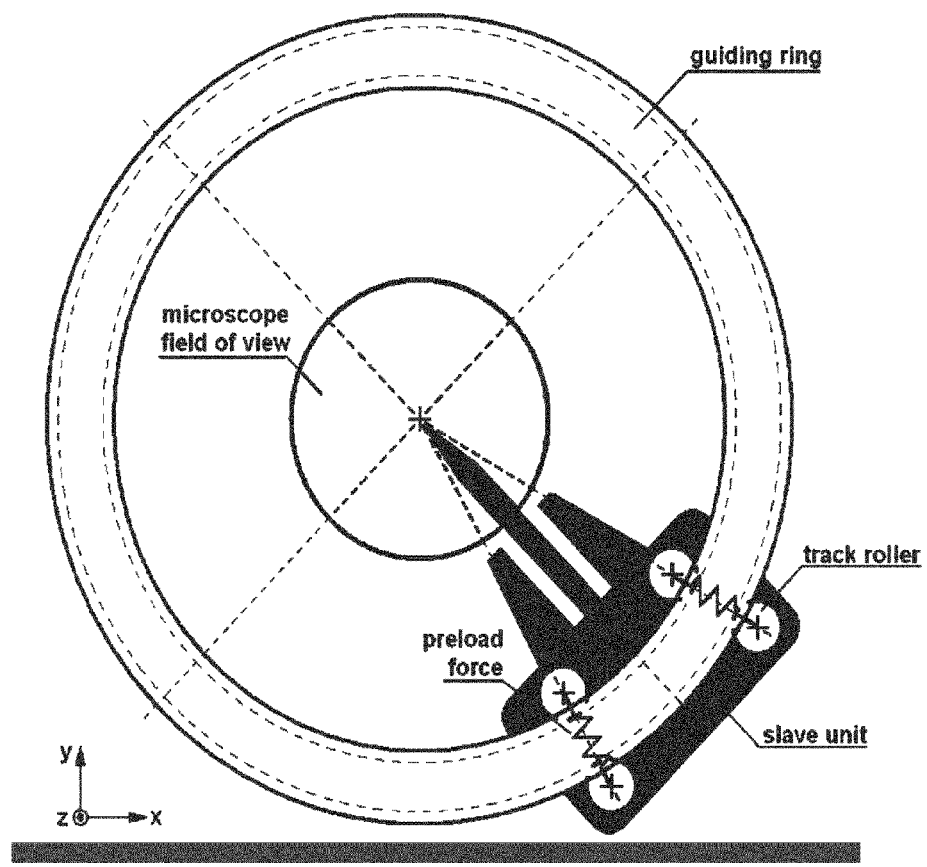
FIG. 7 shows a top view of slave units equipped with track rollers that are guided along a suspension guiding ring, centered with respect to the microscope field of view according to an embodiment of the invention.

By equipping the slave with track rollers, a guiding ring suspension (FIG. 7) can provide a solution. The guiding ring has its center coinciding with the optical axis of the microscope such that upon tangentially moving the slave units, the instrument tip keeps its original radial distance from the operation site.

The ring may be a full circle or a segment or may be composed of several segments of different radii, each of which supporting a slave unit. The ring or ring segments or track rollers can contain an active or passive actuation and measurement system.

Different slave units can be supported by a single ring or ring segment suspension. The user may decide whether an operation requires a single master-slave device (one-handed robotic assistance), two master-slave devices (double-handed robotic assistance) or multiple master slave devices (multi-person robotic assistance).

Slave units can be removed from the suspension either by removing the preload force between the track rollers and the guiding ring (FIG. 7), or by removing the slave unit together with a ring segment.

Furthermore, the suspension has a structure that rigidly connects the ring or ring segment to the ground, defined as any solid object that serves as a position reference for the suspension. Several examples of these are the operating room floor or ceiling or wall, the operating bed side railing or a side table, or the existing microscope support structure. In each case the suspension is detachable.

The suspension structure may further include an integrated microscope system, an additional 6-DOF positioning system to align the guiding ring with the microscope field of view or to align the integrated microscope's field of view with the operation site, or a patient tracking system. This system makes the center of the guiding ring follow any motion induced by the patient, e.g. tremor, pulse or heartbeat, respiration, body rolling. Also, the suspension structure may include a lighting system or a user interface containing a display with information about the status of the system.

Workstation

By creating a system containing a fixed operating plane, suspension and an integrated microscope, a compact single or multi-person workstation can be created.

Figure 8:
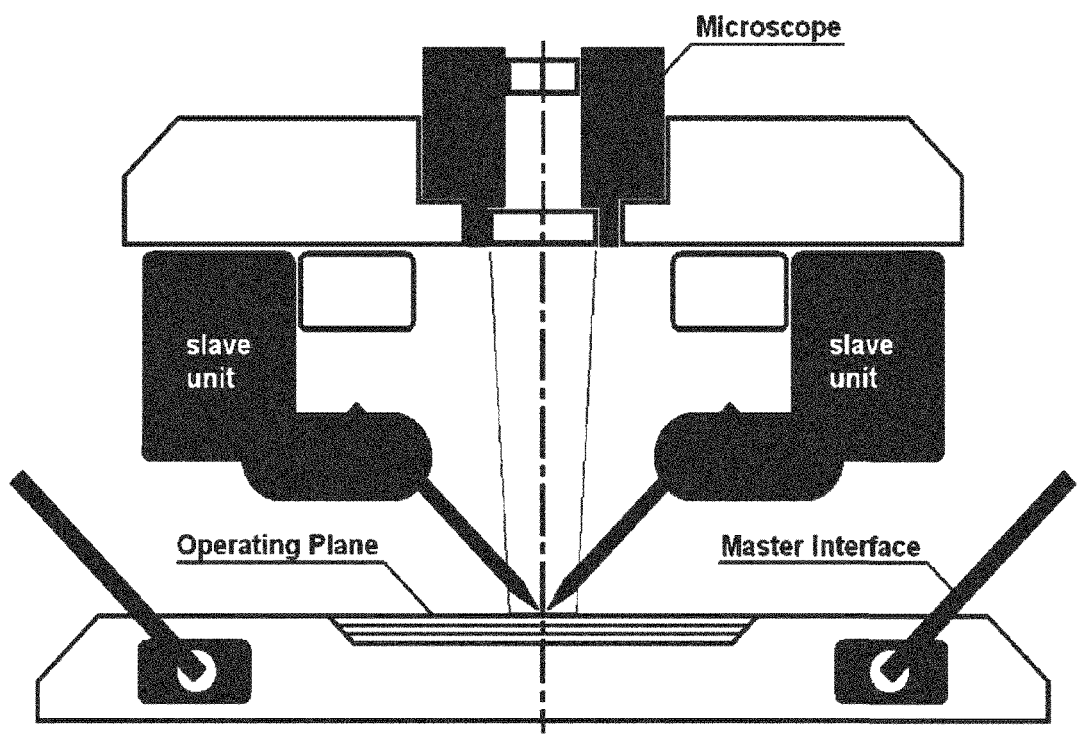
FIG. 8 shows a single-person compact workstation including a fixed operating plane and suspension with an integrated double-handed master-slave system and an integrated microscope according to an embodiment of the invention.

A single-person workstation would include two master-slave systems, which are integrated in the suspension and operating plane structure. The microscope is integrated in the top of the slave suspension (FIG. 8).

For a multi-person workstation the number of slave units and corresponding master interfaces could be increased tangentially along the rim of the workstation, while using the same microscope.

A workstation is especially suitable for single or dual-person tasks where long-term user concentration and a high level of precision are required outside the medical environment.

Differential Module

Each master and slave unit has an identical 6-DOF kinematical design in a balanced parallelogram configuration. The layout and separation of these six degrees of freedom has been chosen such that it is possible to build them up out of three differential gears. Following the parallelogram configuration, these differential gears are placed in serial order.

The differential gears have two opposing driving gears and a driven gear perpendicular to the driving gears. If the driving gears both rotate in similar direction, the driven gear will rotate about the axis of the driving gears as well. If the driving gears rotate in opposite direction, the driven gear will rotate about its own axis.

Figure 9:
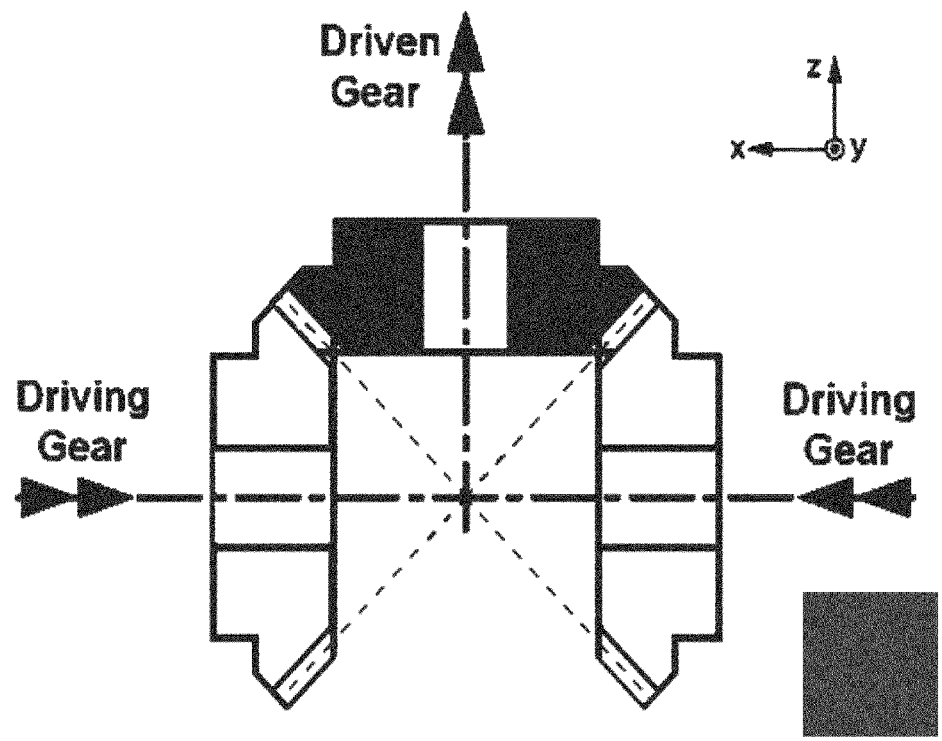
FIG. 9 shows a differential gear according to an embodiment of the invention.

The differential gear may be built up of any type of gear or transmission, i.e. bevel gears (FIG. 9), spur gears, helical gears, hypoid gears, worm gears, crown gears, anti-backlash gears, friction gears, rack and pinion, push or pull rods, elastic hinges, chains, belts or wire transmissions.

Figure 10:
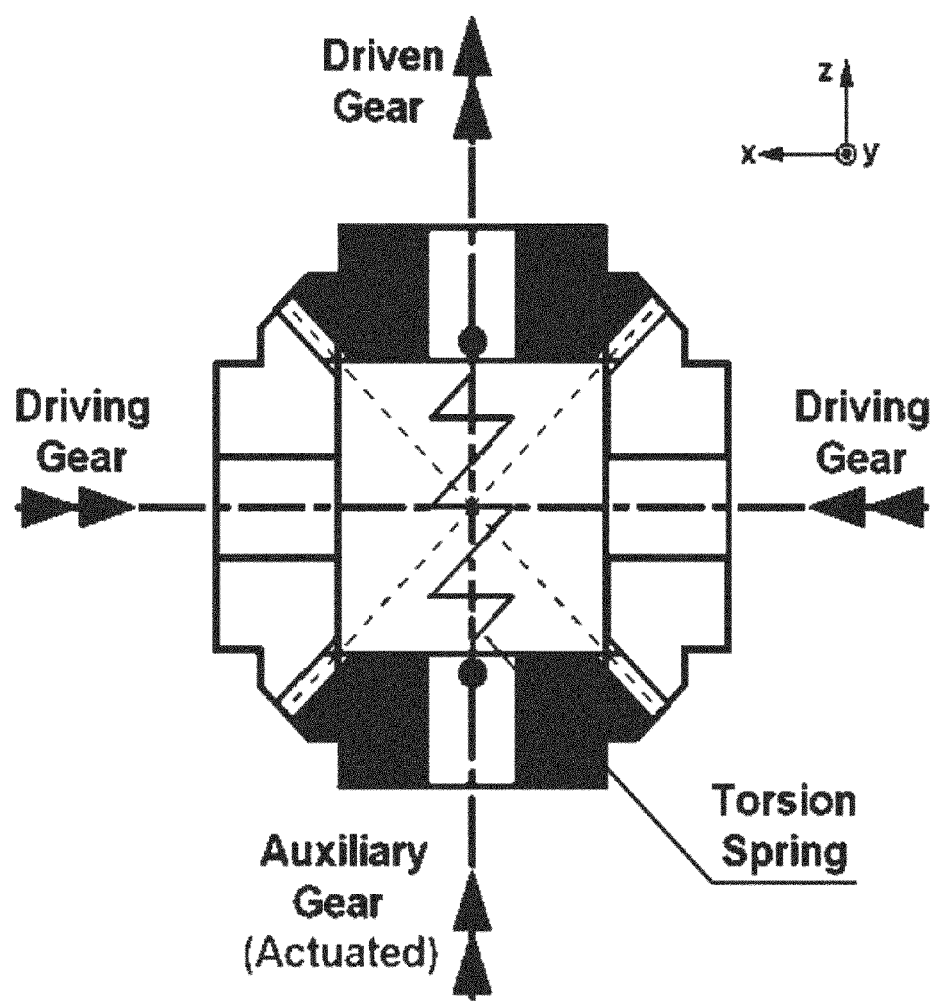
FIG. 10 shows a differential gear with auxiliary gear according to an embodiment of the invention.

The differential gears may have an auxiliary gear that is used to reduce play between the teeth of the driving gears and the driven gear (FIG. 10). The auxiliary gear may be passively controlled and coupled to the driven gear by an elastic or frictional connection, or actively controlled by means of an external actuator.

The differential gears may have a uniform material for all gears, such as steel.

In that case the meshing gear teeth need to be lubricated at all times or the teeth can be coated such that galling and frictional wear is reduced.

The differential gears may have a certain set of material such that meshing gear teeth are always of a different class of material, i.e. metal and plastic. This eliminates the need for lubricants and prevents any form of galling.

Figure 11A:
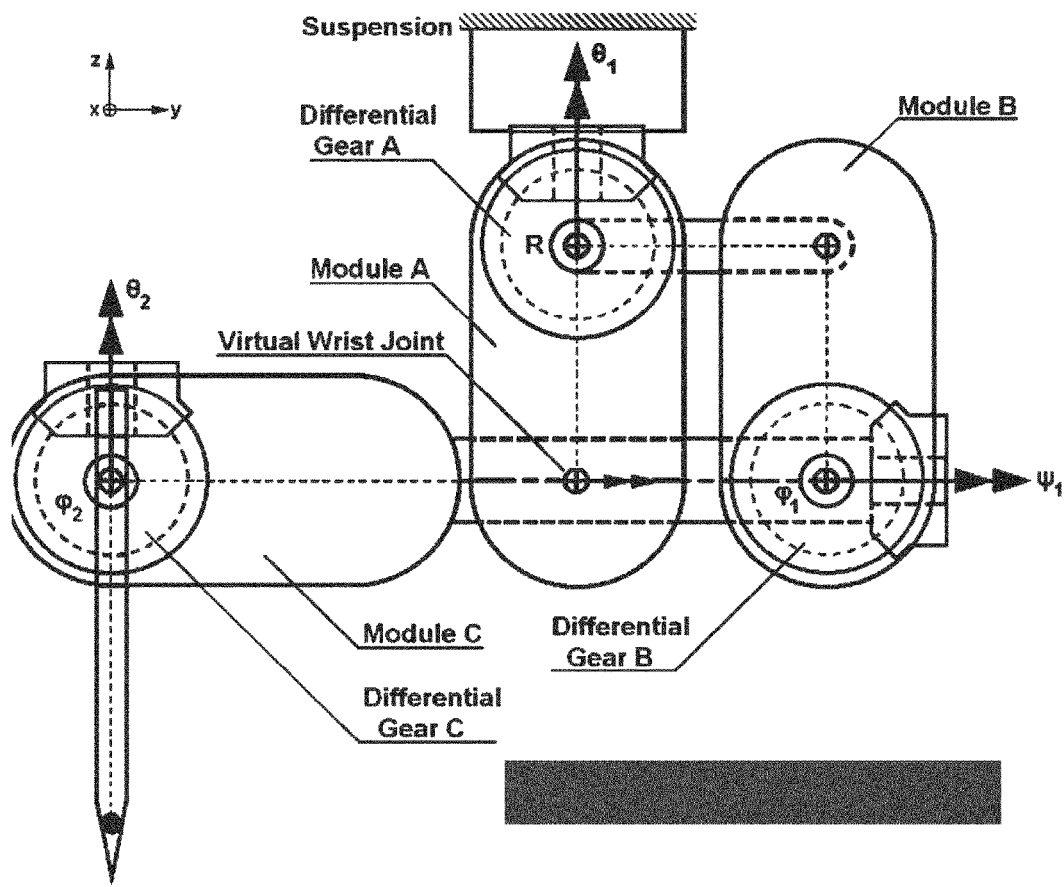
FIGS. 11A-B show each a 6-DOF Configuration by using three differential gears in series according to embodiments of the invention.
Figure 11B:
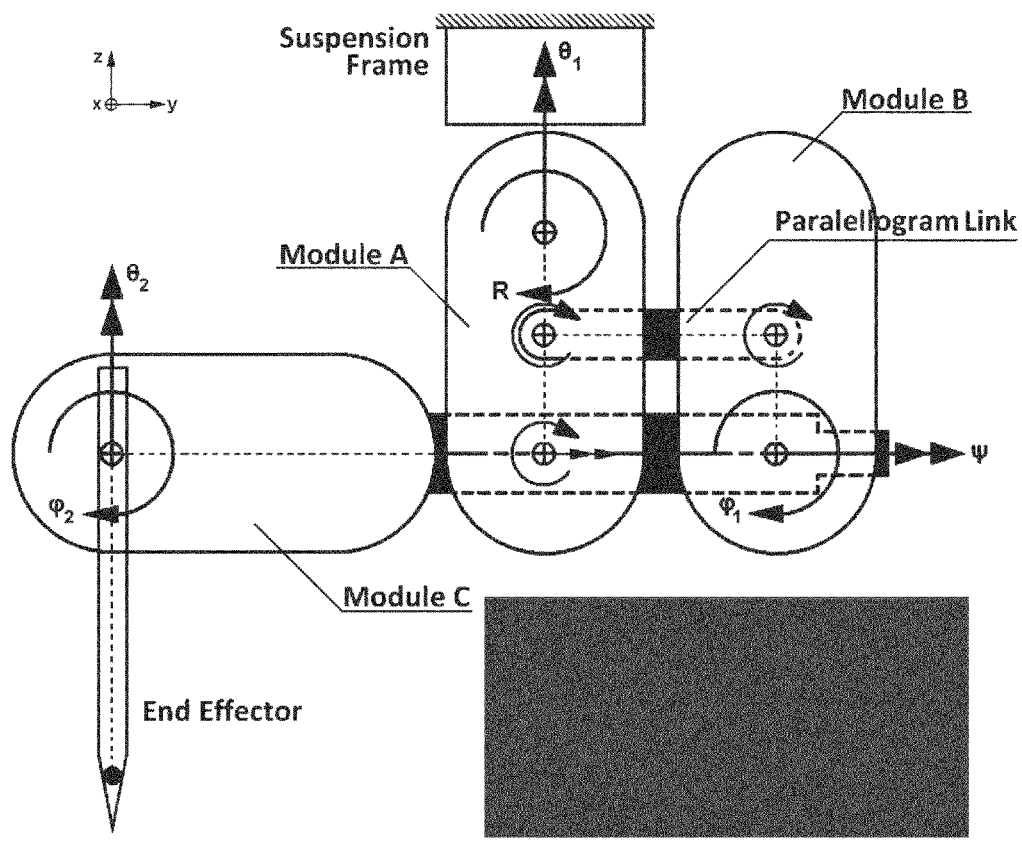

The master and slave units are built up out of three identical modules (module A, B and C), each having a differential gear (FIGS. 11A-B). The modules are rigid bodies and have two independently controlled input shafts that actuate the driving gears of the differential and one output shaft connected to the driven gear.

With respect to FIG. 11A, differential gear A has its output shaft fixed to the suspension such that module A can rotate itself about θ1 and R, thereby translating modules B and C.

Module B has its output shaft rigidly coupled to module C such that an opposite rotation of the driving gears in differential gear B results in module C rotating about ψ1, while a unidirectional rotation of the driving gears results in module C rotating about φ1 translated to the virtual wrist joint.

The output shaft of module C is connected to the instrument shaft, producing rotations θ2 and φ2.

Apart from creating the virtual wrist joint, the parallelogram link connecting modules A and B serves to prevent module B from rotating around ψ1 along with module C. This link may be positioned parallel to ψ1 at any height as long as it symmetrically connects modules A and B.

The differential modules are designed as hollow U-shaped structures, containing all the essential components to make their corresponding differential gears function properly. The component layout inside the modules is symmetrical, such that two halves of the U-shaped module can be taken apart and can function separately as well (without forming the differential gear).

One halve of a differential module is referred to as a differential unit.

Figure 12:
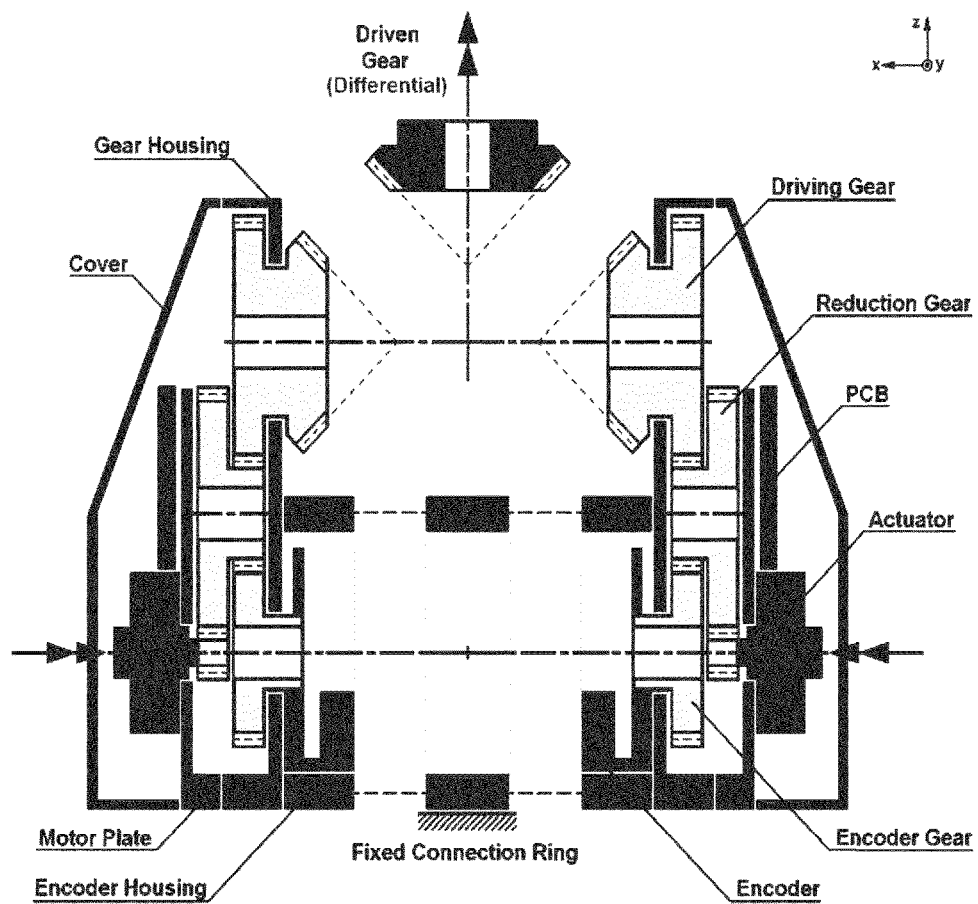
FIG. 12 shows a section of a differential module with two identical differential units connected by a fixed connection ring according to an embodiment of the invention.

A differential unit may contain a driving gear of a differential gear, a transmission or reduction, all the required bearings, an actuator, an encoder, a printed circuit board with a control and processing unit, and a structural housing (FIG. 12).

Two differential units are coupled by fastening eight bolts into a center part, which also forms the connection point to the next differential module (e.g. the shaft connecting modules B and C). This implies that six identical differential units are used for each master or slave unit.

Master-Slave Interaction

The main function of the device is to lower the effective skill capacity required to perform microsurgical tasks, on a physical as well as on a mental level. The device may also be used for micro-scale tasks outside the medical environment, where long-term concentration and precision are required.

The device has been designed in such a way that the slave copies the physiological motions of the human hand holding an instrument. As a consequence, the motions of the slave device will be fully predictable to the operator, i.e. the slave will react intuitively. This is helpful especially for systems using a microscope or camera with a field of view that does not include every moving part of the slave device.

Compared to other robotic systems, the intuitive slave design according to this invention reduces the chance of collision (without taking into account any anti-collision software). Also, since the motion trajectories required to perform a task will be similar to a manual performance, the motions of the slave device are predictable not only to the operator, but also to an assistant. This means that the assistant can actively participate in the operation, either manually or with an extra (pair of) slave device(s).

While the slave devices and their suspension are positioned with respect to the microscope and the operation site, the master devices are detachable and can be positioned freely according to the requirements of the operator. This allows the operator to assume the most ergonomic posture during the operation.

As the operator controls the master device, the input motions are registered by a processor. The processor filters out any high frequency tremor in the input motions, then scales the motion signal to the required scale factor set by the operator. The scaled motion signals are then transmitted to the slave device which performs the motions.

By performing torque feed forward control at the slave device and compared to the actual torque required to complete the motion, a measure for the applied force at the tip of the instrument can be calculated. This signal is then sent back to the master device and delivered to the operator as force feedback.

Figure 13:
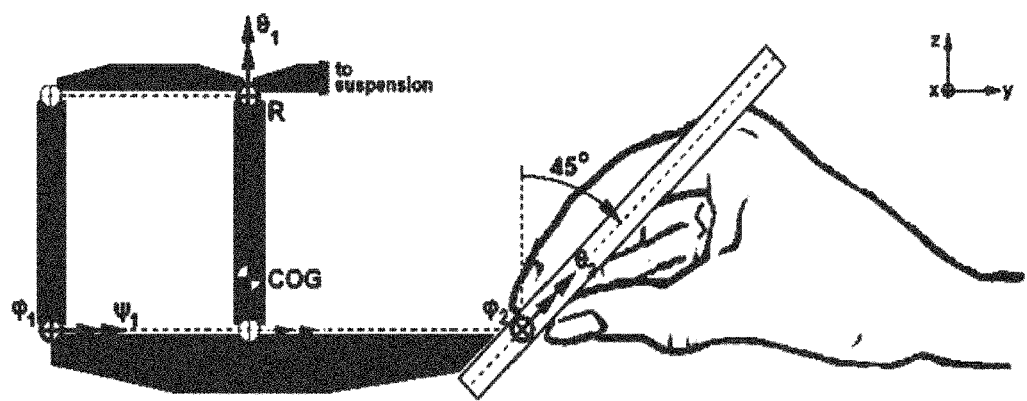
FIG. 13 shows a mechanical layout for master configuration according to an embodiment of the invention.

The master device is equipped with a pen or forceps shaped interface. This has been done to resemble manual operation as closely as possible so that no additional training is required. Since the operator controls the master device close to the base of the interface (FIG. 13), the force feedback is transmitted directly to the operator's hand and will therefore feel realistic.

Master Interface

The pen or forceps shaped interface at the master device can be equipped with an extra internal degree of freedom, e.g. a push button or lever. While the master interface can be moved in six degrees of freedom to control the slave position and orientation, the extra degree of freedom is used to actuate any kind of instrument tip at the slave device (e.g. jaws or scissors).

Figure 14:
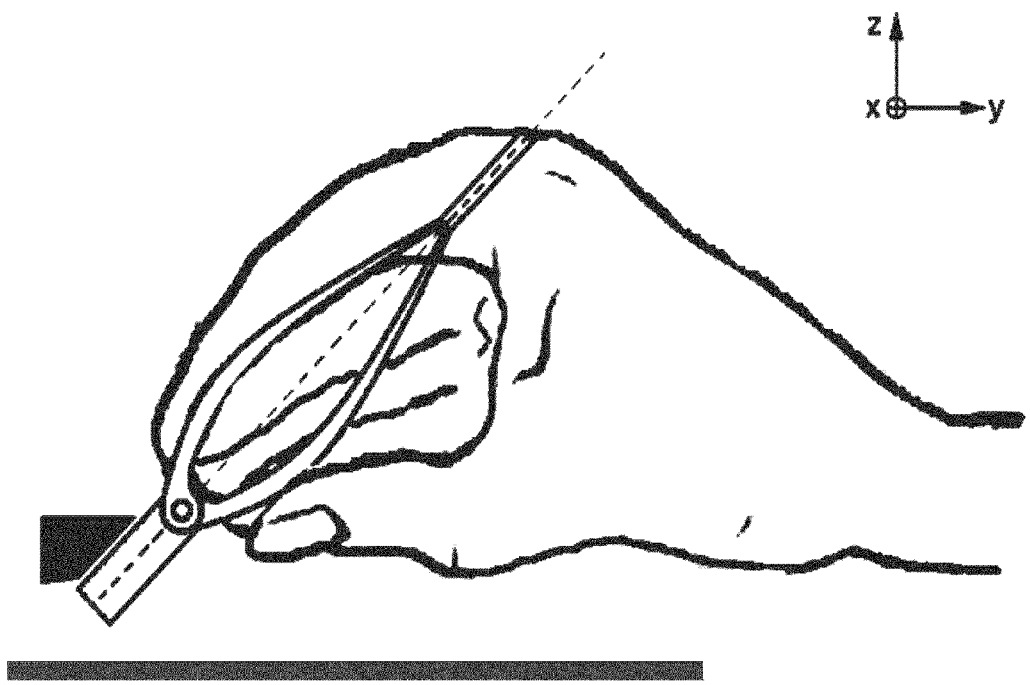
FIG. 14 shows a forceps shaped master interface with 1-DOF internal actuation mechanism according to an embodiment of the invention.

The forceps shaped master interface has two legs that are connected by a hinge at the base of the interface. The hinge is fixed to a rod that is connected to the tip of the master device (FIG. 14).

One of the legs of the interface may be rigidly fixed to the rod, while the other leg can rotate around the hinge. Alternatively, both legs may be able to rotate around the hinge but their rotations are coupled by means of a 1:1 transmission ratio.

At the backside the legs are rigidly coupled. The thinning sections of the legs form a spring which always pushes the legs to their natural position.

Upon pressing the legs together the rotation is measured at the hinge (e.g. a rotary encoder), possibly by using an extended lever system which places the measuring system further away from the operator's hand. The measurement signal is then sent to a processor before it will be sent to the slave device. Force feedback for the master interface will be passive, i.e. the spring at the back of the legs has a stiffness which is chosen such that it resembles the stiffness in actual microsurgical forceps (or needle holder, etc). Again, this is done to give the operator an intuitive feel while using the device. Moreover, when a microsurgical task is done manually the "squeezing force" a surgeon feels is mostly defined by the spring stiffness of the instruments used.

However, the legs can be actuated externally if active force feedback is proven to be required. An actuator mechanism can be placed parallel to the measuring mechanism.

Slave Instruments

The slave device can be equipped with true (i.e. existing) microsurgical instruments, i.e. the same instruments that are used during manual microsurgery. A regular microsurgical instrument set could have five different types of instruments, being a needle holder, straight forceps, curved forceps, dilatation forceps and scissors. All instruments are handled the same way, and are actuated by pressing the two legs together.

Microsurgical instruments are high quality products that can easily be obtained and that already comply with all regulations required in a medical environment. From an economical point of view it is therefore undesirable to design an entirely new set of instruments for the slave device. Moreover, from a safety aspect, for the surgeon or operator it is preferable to be fully acquainted with the slave instruments.

Therefore, the slave device is designed with an end piece that can carry and actuate a true microsurgical instrument. The end piece is positioned and oriented with respect to the operation site in six degrees of freedom by the slave mechanism. Internally, the end piece is equipped with a set of jaws that grab and actuate the microsurgical instruments.

What is claimed:

1. A robotic instrument manipulation device, comprising:
   (a) a first module, wherein a top portion of said first module comprises a first differential gear, wherein a bottom portion of said first module comprises a universal joint, wherein said first differential gear comprises a first driven gear and a first pair of driving gears disposed on opposite sides of said first driven gear, wherein said first pair of driving gears are disposed along a first common axis, wherein said first driven gear comprises a first drive shaft that is fixedly suspended, wherein said first module rotates about an axis of said first drive shaft when said first pair of driving gears counter rotate, wherein said first driven gear rotates said first module about said first common axis when said first pair of driving gears co-rotate;
   (b) a second module, wherein a top portion of said first module is pivotably connected to a top portion of said second module, wherein said pivotable connection comprises a first module pivotable connection and a second module pivotable connection, wherein a bottom portion of said second module comprises a second differential gear, wherein said second differential gear comprises a second driven gear and a second pair of driving gears disposed on opposite sides of said second driven gear, wherein said second pair of driving gears are disposed along a second common axis, wherein said second driven gear comprises a second drive shaft that rotates about an axis of said second drive shaft when said second pair of driving gears counter rotate, wherein said second drive shaft rotates about said second common axis when said second pair of driving gears co-rotate; and (c) a third module, wherein said third module comprises a third differential gear disposed at a distal end of said third module, wherein a distal end of said second drive shaft is fixedly connected to a proximal end of said third module, wherein a mid-portion of said second drive shaft is connected to said universal joint, wherein said third differential gear comprises a third driven gear and a third pair of driving gears disposed on opposite sides of said third driven gear, wherein said third pair of driving gears are disposed along a third common axis, wherein said third driven gear comprises an instrument, wherein said instrument rotates about an instrument longitudinal axis when said third pair of driving gears counter rotate, wherein said instrument rotates about said third common axis when said third pair of driving gears co-rotate, wherein said first module pivotable connection, said second module pivotable connection, said second common axis and said universal joint form a parallelogram.

2. The robotic instrument manipulation device as set forth in claim 1, wherein said robotic instrument manipulation device comprises an actuator, wherein said actuator operates a tool disposed at a distal end of said instrument.

3. The robotic instrument manipulation device as set forth in claim 1, wherein said robotic instrument manipulation device comprises a center of gravity that is proximal to said universal joint.

4. The robotic instrument manipulation device as set forth in claim 1, wherein said robotic instrument manipulation device is remotely controlled according to a master-slave system.

5. The robotic instrument manipulation device as set forth in claim 4, wherein a master device in said master-slave system comprises a second robotic instrument manipulation device that is operated using a tool on said instrument.

6. The robotic instrument manipulation device as set forth in claim 1, wherein said pivotal connection between said top portion of said first module and said top portion of said second module comprises a rigid link of said parallelogram.

7. The robotic instrument manipulation device as set forth in claim 1, wherein said first module pivotal connection comprises said first common axis of said first differential gear.

8. The robotic instrument manipulation device as set forth in claim 7, wherein said pivotal connection between said top portion of said first module and said top portion of said second module comprises a rigid link of said parallelogram, wherein said rigid link is perpendicular to said first shaft.

9. The robotic instrument manipulation device as set forth in claim 1, wherein said first common axis is perpendicular to said first drive shaft.

10. The robotic instrument manipulation device as set forth in claim 1, wherein said second common axis is perpendicular to said second drive shaft.

11. The robotic instrument manipulation device as set forth in claim 1, wherein said third common axis is perpendicular to said third drive shaft.

* * * * *